(12) United States Patent
Christensen et al.

(10) Patent No.: US 8,235,971 B2
(45) Date of Patent: Aug. 7, 2012

(54) CATHETER CONNECTION SYSTEMS

(75) Inventors: Mark A. Christensen, Salt Lake City, UT (US); William R. Barron, Riverton, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 12/879,673

(22) Filed: Sep. 10, 2010

(65) Prior Publication Data

US 2011/0009849 A1  Jan. 13, 2011

Related U.S. Application Data

(63) Continuation of application No. 11/535,245, filed on Sep. 26, 2006.

(60) Provisional application No. 60/720,443, filed on Sep. 26, 2005.

(51) Int. Cl.
*A61M 25/16* (2006.01)

(52) U.S. Cl. ........ 604/536; 604/533; 604/534; 604/535; 604/537

(58) Field of Classification Search .................. 604/256, 604/533, 535–537, 540, 246, 535–53, 534
See application file for complete search history.

(56) References Cited

U.S. PATENT DOCUMENTS

| | | | |
|---|---|---|---|
| 3,003,500 A | 10/1961 | Barton et al. | |
| 3,021,841 A | 2/1962 | Burke | |
| 3,115,138 A | 12/1963 | McElvenny et al. | |
| 3,223,610 A | 12/1965 | Inoue | |
| 3,233,610 A | 2/1966 | Wade | |
| 3,241,554 A | 3/1966 | Coanda | |
| 3,253,594 A | 5/1966 | Matthews | |
| 3,312,221 A | 4/1967 | Overment | |
| 3,315,802 A | 4/1967 | Lonholdt et al. | |
| 3,363,626 A | 1/1968 | Bidwell et al. | |
| 3,376,868 A | 4/1968 | Mondiadis | |
| 3,417,750 A | 12/1968 | Carson | |
| 3,419,010 A | 12/1968 | Williamson | |
| 3,459,189 A | 8/1969 | Alley | |
| 3,487,837 A | 1/1970 | Petersen | |
| 3,542,026 A | 12/1970 | Bledsoe | |
| 3,554,580 A | 1/1971 | Goyke | |
| 3,566,875 A | 3/1971 | Stoehr | |

(Continued)

FOREIGN PATENT DOCUMENTS

DE    1616493 A1    6/1971

(Continued)

OTHER PUBLICATIONS

"Experimental Plerueodesis in Rabbits Induced by Silver Nitrate or Talc," ASAP, vol. 199, No. 5, p. 1516, May 1, 2001.
"Management of Malignant Pleural Effusions." Am. J. Respir. Crit. Care Med., vol. 165, No. 5, pp. 1987-2001, 2000.
"Pleural Disease—Diagnosis and Management," The Practitioner, p. 412, May 1999.

(Continued)

*Primary Examiner* — Kevin C Sirmons
*Assistant Examiner* — Bradley Thomas, Jr.
(74) *Attorney, Agent, or Firm* — Rutan & Tucker, LLP (57) ABSTRACT

A catheter connection system is disclosed. In one embodiment, a catheter connection system may include at least two components and a deformable sealing element positioned between the at least two components configured to allow, upon deformation, fluid flow through the at least two components. In another embodiment, the catheter connection system may include a sealing element positioned between at least two components, wherein the components are coupled to one another by a locking member.

8 Claims, 4 Drawing Sheets

U.S. PATENT DOCUMENTS

| | | |
|---|---|---|
| 3,572,340 A | 3/1971 | Lloyd et al. |
| 3,650,507 A | 3/1972 | Nyberg et al. |
| 3,680,562 A | 8/1972 | Wittes et al. |
| 3,683,929 A | 8/1972 | Holter |
| 3,742,952 A | 7/1973 | Magers et al. |
| 3,752,158 A | 8/1973 | Kariher |
| 3,768,476 A | 10/1973 | Raitto |
| 3,774,611 A | 11/1973 | Tussey et al. |
| 3,777,757 A | 12/1973 | Gray et al. |
| 3,783,870 A | 1/1974 | Schachet |
| 3,820,546 A | 6/1974 | Chittenden et al. |
| 3,853,127 A | 12/1974 | Spademan |
| 3,920,023 A | 11/1975 | Dye et al. |
| 3,960,153 A | 6/1976 | Carey et al. |
| 3,982,546 A | 9/1976 | Friend |
| 4,022,209 A | 5/1977 | Nehring |
| 4,029,095 A | 6/1977 | Pena |
| 4,105,031 A | 8/1978 | Kurtz et al. |
| 4,112,949 A | 9/1978 | Rosenthal et al. |
| 4,116,366 A | 9/1978 | Takenakashima et al. |
| 4,120,715 A | 10/1978 | Ockwell et al. |
| 4,136,696 A | 1/1979 | Nehring |
| 4,143,853 A | 3/1979 | Abramson |
| 4,153,058 A | 5/1979 | Nehme |
| 4,170,300 A | 10/1979 | Pick |
| 4,174,053 A | 11/1979 | Shimizu |
| 4,187,848 A | 2/1980 | Taylor |
| 4,203,445 A | 5/1980 | Jessup et al. |
| 4,214,593 A | 7/1980 | Imbruce et al. |
| 4,257,629 A | 3/1981 | Maple et al. |
| 4,265,848 A | 5/1981 | Rusch et al. |
| 4,266,355 A | 5/1981 | Moss |
| 4,266,545 A | 5/1981 | Moss |
| 4,310,104 A | 1/1982 | Takatsuki |
| 4,315,513 A | 2/1982 | Nawash et al. |
| 4,334,551 A | 6/1982 | Pfister |
| 4,341,212 A | 7/1982 | Medwid |
| D267,433 S | 12/1982 | Pageau |
| 4,364,395 A | 12/1982 | Redmond et al. |
| D267,815 S | 2/1983 | Elliott et al. |
| 4,382,442 A | 5/1983 | Jones |
| 4,392,858 A | 7/1983 | George et al. |
| 4,393,873 A | 7/1983 | Nawash et al. |
| 4,427,425 A | 1/1984 | Briggs et al. |
| 4,433,973 A | 2/1984 | Kurtz et al. |
| 4,439,190 A | 3/1984 | Protzmann et al. |
| 4,447,235 A | 5/1984 | Clarke |
| 4,455,141 A | 6/1984 | Todd |
| 4,464,168 A | 8/1984 | Redmond et al. |
| 4,475,904 A | 10/1984 | Wang |
| 4,479,818 A | 10/1984 | Briggs et al. |
| 4,490,003 A | 12/1984 | Robinson |
| 4,496,464 A | 1/1985 | Hensley |
| 4,501,363 A | 2/1985 | Isbey, Jr. |
| 4,511,163 A | 4/1985 | Harris et al. |
| 4,512,771 A | 4/1985 | Norton |
| 4,525,167 A | 6/1985 | Goldberg et al. |
| 4,543,100 A | 9/1985 | Brodsky |
| 4,564,222 A | 1/1986 | Loker et al. |
| 4,569,674 A | 2/1986 | Phillips et al. |
| 4,605,400 A | 8/1986 | Kurtz et al. |
| 4,610,469 A | 9/1986 | Wolff-Mooij |
| 4,610,671 A | 9/1986 | Luther |
| 4,620,846 A | 11/1986 | Goldberg et al. |
| 4,643,720 A | 2/1987 | Lanciano |
| 4,648,870 A | 3/1987 | Goldberg et al. |
| 4,666,433 A | 5/1987 | Parks |
| 4,669,463 A | 6/1987 | McConnell |
| 4,673,398 A | 6/1987 | Turner et al. |
| 4,675,020 A | 6/1987 | McPhee |
| 4,681,571 A | 7/1987 | Nehring |
| 4,685,901 A | 8/1987 | Parks |
| 4,685,908 A | 8/1987 | Kurtz |
| 4,701,163 A | 10/1987 | Parks |
| 4,702,733 A | 10/1987 | Wright et al. |
| 4,706,830 A | 11/1987 | Wareing et al. |
| 4,722,735 A | 2/1988 | Brodmann |
| 4,738,671 A | 4/1988 | Elliott et al. |
| 4,740,202 A | 4/1988 | Stacey et al. |
| 4,741,678 A | 5/1988 | Nehring |
| 4,747,843 A | 5/1988 | Felix et al. |
| 4,747,844 A | 5/1988 | Elliott |
| 4,752,292 A | 6/1988 | Lopez et al. |
| 4,758,238 A | 7/1988 | Sundblom et al. |
| 4,781,674 A | 11/1988 | Redmond et al. |
| 4,790,567 A | 12/1988 | Kawano et al. |
| 4,809,679 A | 3/1989 | Shimonaka et al. |
| 4,813,929 A | 3/1989 | Semrad |
| 4,820,288 A | 4/1989 | Isono |
| 4,832,442 A | 5/1989 | Pappas |
| 4,834,702 A | 5/1989 | Rocco |
| 4,844,087 A | 7/1989 | Garg |
| 4,850,955 A | 7/1989 | Newkirk |
| 4,857,042 A | 8/1989 | Schneider |
| 4,863,593 A | 9/1989 | Quick |
| 4,867,740 A | 9/1989 | East |
| 4,874,377 A | 10/1989 | Newgard et al. |
| 4,883,474 A | 11/1989 | Sheridan et al. |
| 4,883,476 A | 11/1989 | Kurtz et al. |
| 4,921,488 A | 5/1990 | Maitz et al. |
| 4,929,235 A | 5/1990 | Merry et al. |
| 4,930,997 A | 6/1990 | Bennett |
| 4,944,732 A | 7/1990 | Russo |
| 4,946,448 A | 8/1990 | Richmond |
| 4,946,449 A | 8/1990 | Davis, Jr. |
| 4,949,756 A | 8/1990 | Melinyshyn et al. |
| 4,950,256 A | 8/1990 | Luther et al. |
| 4,960,412 A | 10/1990 | Fink |
| 4,966,197 A | 10/1990 | Jaron et al. |
| 4,968,294 A | 11/1990 | Salama |
| 4,969,879 A | 11/1990 | Lichte |
| 4,969,890 A | 11/1990 | Sugita et al. |
| 4,973,311 A | 11/1990 | Iwakoshi et al. |
| 4,995,864 A | 2/1991 | Bartholomew et al. |
| 5,002,529 A | 3/1991 | Cunningham |
| 5,009,636 A | 4/1991 | Wortley et al. |
| 5,019,096 A | 5/1991 | Fox, Jr. et al. |
| 5,037,403 A | 8/1991 | Garcia |
| 5,052,998 A | 10/1991 | Zimmon |
| 5,053,014 A | 10/1991 | Van Heugten |
| 5,057,084 A | 10/1991 | Ensminger et al. |
| 5,060,833 A | 10/1991 | Edison et al. |
| 5,061,255 A | 10/1991 | Greenfeld et al. |
| 5,064,416 A | 11/1991 | Newgard et al. |
| 5,078,677 A | 1/1992 | Gentelia et al. |
| 5,078,689 A | 1/1992 | Keller |
| 5,078,699 A | 1/1992 | Haber et al. |
| 5,085,349 A | 2/1992 | Fawcett |
| 5,092,850 A | 3/1992 | Buma |
| 5,098,405 A | 3/1992 | Peterson et al. |
| 5,100,394 A | 3/1992 | Dudar et al. |
| 5,102,404 A | 4/1992 | Goldberg et al. |
| 5,106,054 A | 4/1992 | Mollenauer et al. |
| 5,112,323 A | 5/1992 | Winkler et al. |
| 5,137,524 A | 8/1992 | Lynn et al. |
| 5,141,499 A | 8/1992 | Zappacosta |
| 5,156,597 A | 10/1992 | Verreet et al. |
| 5,165,953 A | 11/1992 | Shlenker et al. |
| 5,188,622 A | 2/1993 | Muller et al. |
| 5,199,946 A | 4/1993 | Abramowitz |
| 5,207,655 A | 5/1993 | Sheridan |
| 5,215,538 A | 6/1993 | Larkin |
| 5,234,454 A | 8/1993 | Bangs |
| 5,238,217 A | 8/1993 | Fell |
| 5,251,873 A | 10/1993 | Atkinson et al. |
| 5,261,897 A | 11/1993 | Kurtz et al. |
| 5,269,771 A | 12/1993 | Thomas et al. |
| 5,279,551 A | 1/1994 | James |
| 5,295,657 A | 3/1994 | Atkinson |
| 5,295,658 A | 3/1994 | Atkinson et al. |
| 5,300,034 A | 4/1994 | Behnke et al. |
| 5,300,048 A | 4/1994 | Drewes, Jr. et al. |
| 5,304,121 A | 4/1994 | Sahatjian |
| 5,320,110 A | 6/1994 | Wang |
| 5,322,518 A | 6/1994 | Schneider et al. |
| 5,334,159 A | 8/1994 | Turkel |
| 5,334,166 A | 8/1994 | Palestrant |

| | | | | | | |
|---|---|---|---|---|---|---|
| 5,344,401 | A | 9/1994 | Radisch et al. | 6,024,731 | A | 2/2000 | Seddon et al. |
| 5,352,198 | A | 10/1994 | Goldenberg et al. | 6,025,044 | A | 2/2000 | Campbell et al. |
| 5,356,391 | A | 10/1994 | Stewart | 6,027,779 | A | 2/2000 | Campbell et al. |
| 5,360,413 | A | 11/1994 | Leason et al. | 6,027,811 | A | 2/2000 | Campbell et al. |
| 5,390,898 | A | 2/1995 | Smedley et al. | 6,029,946 | A | 2/2000 | Doyle |
| 5,395,651 | A | 3/1995 | Sodervall et al. | 6,039,302 | A | 3/2000 | Cote, Sr. et al. |
| 5,399,165 | A | 3/1995 | Paul, Jr. | 6,039,714 | A | 3/2000 | Cracauer et al. |
| 5,401,245 | A | 3/1995 | Haining | 6,068,011 | A | 5/2000 | Paradis |
| 5,405,331 | A | 4/1995 | Behnke et al. | 6,070,767 | A | 6/2000 | Gardner et al. |
| 5,423,334 | A | 6/1995 | Jordan | 6,079,444 | A | 6/2000 | Harris et al. |
| 5,435,470 | A | 7/1995 | Kim | 6,089,541 | A | 7/2000 | Weinheimer et al. |
| 5,437,900 | A | 8/1995 | Kuzowski | 6,093,154 | A | 7/2000 | Burek et al. |
| 5,456,675 | A | 10/1995 | Wolbring et al. | 6,103,695 | A | 8/2000 | Lane et al. |
| 5,465,857 | A | 11/1995 | Yang | 6,106,502 | A | 8/2000 | Richmond |
| 5,470,319 | A | 11/1995 | Mayer | 6,106,503 | A | 8/2000 | Pfeiderer et al. |
| 5,472,325 | A | 12/1995 | Svendsen et al. | 6,113,068 | A | 9/2000 | Ryan |
| 5,472,435 | A | 12/1995 | Sutton | 6,117,114 | A | 9/2000 | Paradis |
| 5,480,392 | A | 1/1996 | Mous | 6,129,699 | A | 10/2000 | Haight et al. |
| 5,484,401 | A | 1/1996 | Rodriguez et al. | 6,129,750 | A | 10/2000 | Tockman et al. |
| 5,489,269 | A | 2/1996 | Aldrich et al. | 6,132,403 | A | 10/2000 | Lopez |
| 5,492,304 | A | 2/1996 | Smith et al. | 6,132,407 | A | 10/2000 | Genese et al. |
| 5,496,299 | A | 3/1996 | Felix et al. | 6,149,129 | A | 11/2000 | Harris et al. |
| 5,501,426 | A | 3/1996 | Atkinson et al. | 6,156,004 | A | 12/2000 | Tremaine et al. |
| 5,507,733 | A | 4/1996 | Larkin et al. | 6,165,217 | A | 12/2000 | Hayes |
| 5,507,847 | A | 4/1996 | George et al. | 6,168,137 | B1 | 1/2001 | Paradis |
| 5,509,433 | A | 4/1996 | Paradis | 6,170,800 | B1 | 1/2001 | Meloul et al. |
| 5,509,909 | A | 4/1996 | Moy | 6,171,287 | B1 | 1/2001 | Lynn et al. |
| 5,509,912 | A | 4/1996 | Vaillancourt et al. | 6,193,682 | B1 | 2/2001 | Ahmed |
| 5,514,117 | A | 5/1996 | Lynn | 6,196,992 | B1 | 3/2001 | Keilman et al. |
| 5,520,665 | A | 5/1996 | Fleetwood et al. | 6,200,292 | B1 | 3/2001 | French et al. |
| 5,529,278 | A | 6/1996 | Weldon et al. | 6,217,556 | B1 | 4/2001 | Ellingson et al. |
| 5,535,785 | A | 7/1996 | Werge et al. | 6,221,425 | B1 | 4/2001 | Michal et al. |
| 5,540,661 | A | 7/1996 | Tomisaka et al. | 6,234,992 | B1 | 5/2001 | Haight et al. |
| 5,556,387 | A | 9/1996 | Mollenauer et al. | 6,245,048 | B1 | 6/2001 | Fangrow, Jr. et al. |
| 5,573,516 | A | 11/1996 | Tyner | 6,254,061 | B1 | 7/2001 | Levine et al. |
| 5,576,072 | A | 11/1996 | Hostettler et al. | 6,254,581 | B1 | 7/2001 | Scott |
| 5,628,908 | A | 5/1997 | Kamen et al. | 6,261,282 | B1 | 7/2001 | Jepson et al. |
| 5,636,875 | A | 6/1997 | Wasser et al. | 6,283,949 | B1 | 9/2001 | Roorda |
| 5,662,960 | A | 9/1997 | Hostettler et al. | 6,287,285 | B1 | 9/2001 | Michal et al. |
| 5,674,192 | A | 10/1997 | Sahatjian et al. | 6,293,929 | B1 | 9/2001 | Smith et al. |
| 5,676,346 | A | 10/1997 | Leinsing | 6,299,131 | B1 | 10/2001 | Ryan |
| D385,889 | S | 11/1997 | Kullas et al. | 6,299,593 | B1 | 10/2001 | Wakabayashi |
| 5,685,866 | A | 11/1997 | Lopez | 6,309,423 | B2 | 10/2001 | Hayes |
| 5,690,612 | A * | 11/1997 | Lopez et al. ............ 604/95.05 | 6,328,765 | B1 | 12/2001 | Hardwick et al. |
| 5,701,934 | A | 12/1997 | Kuran et al. | 6,332,892 | B1 | 12/2001 | Desmond, III et al. |
| 5,709,672 | A | 1/1998 | Illner | 6,344,033 | B1 * | 2/2002 | Jepson et al. ............ 604/256 |
| 5,725,506 | A | 3/1998 | Freeman et al. | 6,375,024 | B1 | 4/2002 | Park |
| 5,727,714 | A | 3/1998 | Fawcett | 6,391,009 | B1 | 5/2002 | Crosa Dorado et al. |
| 5,733,496 | A | 3/1998 | Avellanet | 6,409,716 | B1 | 6/2002 | Sahatjian et al. |
| 5,735,826 | A | 4/1998 | Richmond | 6,428,520 | B1 | 8/2002 | Lopez et al. |
| 5,738,144 | A | 4/1998 | Rogers | 6,447,473 | B1 | 9/2002 | Levine et al. |
| 5,738,656 | A | 4/1998 | Wagner et al. | 6,482,190 | B1 | 11/2002 | Genese et al. |
| 5,745,719 | A | 4/1998 | Falcon et al. | 6,491,668 | B1 | 12/2002 | Paradis |
| 5,746,719 | A | 5/1998 | Farra et al. | 6,500,164 | B1 | 12/2002 | Turner et al. |
| 5,776,119 | A | 7/1998 | Bilbo et al. | 6,530,951 | B1 | 3/2003 | Bates et al. |
| 5,792,098 | A | 8/1998 | Felix et al. | 6,541,116 | B2 | 4/2003 | Michal et al. |
| 5,792,108 | A | 8/1998 | Felix et al. | 6,551,267 | B1 | 4/2003 | Cohen et al. |
| 5,807,348 | A | 9/1998 | Zinger et al. | 6,554,808 | B1 | 4/2003 | Cook |
| 5,810,792 | A | 9/1998 | Fangrow, Jr. et al. | RE38,145 | E | 6/2003 | Lynn |
| 5,813,597 | A | 9/1998 | Wakevainen | 6,626,418 | B2 | 9/2003 | Kiehne et al. |
| 5,814,024 | A | 9/1998 | Thompson et al. | 6,635,020 | B2 | 10/2003 | Tripp, Jr. et al. |
| 5,823,961 | A | 10/1998 | Fields et al. | 6,637,726 | B1 | 10/2003 | Yamamoto |
| 5,830,185 | A | 11/1998 | Block, Jr. | 6,641,562 | B1 | 11/2003 | Peterson |
| 5,839,715 | A | 11/1998 | Leinsing | 6,641,574 | B2 | 11/2003 | Badia Segura et al. |
| 5,873,853 | A | 2/1999 | Keilman et al. | 6,645,547 | B1 | 11/2003 | Shekalim et al. |
| 5,904,334 | A | 5/1999 | Grunert et al. | 6,651,956 | B2 | 11/2003 | Miller |
| 5,937,885 | A | 8/1999 | Sampson | 6,652,484 | B1 | 11/2003 | Hunckler et al. |
| 5,938,176 | A | 8/1999 | Falconer | 6,655,655 | B1 | 12/2003 | Matkovich et al. |
| 5,947,953 | A | 9/1999 | Ash et al. | 6,656,517 | B2 | 12/2003 | Michal et al. |
| 5,954,706 | A | 9/1999 | Sahatjian | 6,665,888 | B1 | 12/2003 | Kwak |
| 5,957,898 | A | 9/1999 | Jepson et al. | 6,669,681 | B2 | 12/2003 | Jepson et al. |
| 5,957,912 | A | 9/1999 | Heitzmann | 6,673,049 | B2 | 1/2004 | Hommann et al. |
| 5,961,497 | A | 10/1999 | Larkin | 6,673,051 | B2 | 1/2004 | Flinchbaugh |
| 5,971,357 | A | 10/1999 | Denton et al. | 6,695,817 | B1 | 2/2004 | Fangrow, Jr. |
| 5,972,441 | A | 10/1999 | Campbell et al. | 6,699,213 | B1 | 3/2004 | Annis et al. |
| 5,976,650 | A | 11/1999 | Campbell et al. | 6,706,022 | B1 | 3/2004 | Leinsing et al. |
| 5,984,891 | A | 11/1999 | Keilman et al. | 6,708,950 | B2 | 3/2004 | Christensen et al. |
| 5,997,486 | A | 12/1999 | Burek et al. | 6,719,991 | B2 | 4/2004 | Darouiche et al. |
| 6,001,079 | A | 12/1999 | Pourchez | 6,726,672 | B1 | 4/2004 | Hanly et al. |

| | | |
|---|---|---|
| 6,733,000 B2 | 5/2004 | McCarty et al. |
| 6,745,998 B2 | 6/2004 | Doyle |
| 6,780,497 B1 | 8/2004 | Walter |
| 6,802,836 B2 | 10/2004 | Bouphavichith et al. |
| 6,808,161 B1 | 10/2004 | Hishikawa |
| D500,132 S | 12/2004 | Peterson et al. |
| D500,133 S | 12/2004 | Peterson et al. |
| D500,552 S | 1/2005 | Peterson et al. |
| D500,853 S | 1/2005 | Peterson et al. |
| 6,840,501 B2 | 1/2005 | Doyle |
| 6,849,061 B2 | 2/2005 | Wagner |
| 6,896,665 B2 | 5/2005 | Picha et al. |
| 6,897,349 B2 | 5/2005 | Gibbins et al. |
| 6,916,379 B2 | 7/2005 | Shekalim et al. |
| 6,936,031 B2 | 8/2005 | Caleffi |
| 6,972,001 B2 | 12/2005 | Emig et al. |
| 6,994,315 B2 | 2/2006 | Ryan et al. |
| 6,994,325 B2 | 2/2006 | Riedl |
| 7,004,923 B2 | 2/2006 | Deniega et al. |
| 7,004,934 B2 | 2/2006 | Vaillancourt |
| 7,008,407 B1 | 3/2006 | Kamp |
| 7,044,441 B2 | 5/2006 | Doyle |
| 7,048,724 B2 | 5/2006 | Grossman et al. |
| 7,048,962 B2 | 5/2006 | Shekalim et al. |
| 7,052,603 B2 | 5/2006 | Schick |
| 7,090,191 B2 | 8/2006 | Matkovich et al. |
| 7,094,218 B2 | 8/2006 | Rome et al. |
| 7,100,890 B2 | 9/2006 | Cote, Sr. et al. |
| 7,101,353 B2 | 9/2006 | Lui et al. |
| 7,112,177 B2 | 9/2006 | Christensen et al. |
| 7,150,740 B2 | 12/2006 | Bennett et al. |
| 7,165,568 B2 | 1/2007 | Kessell et al. |
| 7,179,244 B2 | 2/2007 | Smith et al. |
| 7,184,825 B2 | 2/2007 | Leinsing et al. |
| 7,303,553 B2 | 12/2007 | Ott |
| 7,311,690 B2 | 12/2007 | Burnett |
| 7,312,304 B2 | 12/2007 | Coy et al. |
| 7,314,061 B2 | 1/2008 | Peppel |
| 7,320,674 B2 | 1/2008 | Ruddell et al. |
| 7,341,240 B2 | 3/2008 | Ciesielka |
| 7,377,915 B2 | 5/2008 | Rasmussen et al. |
| 7,383,073 B1 | 6/2008 | Abovitz et al. |
| 7,396,348 B2 * | 7/2008 | Newton et al. ............... 604/256 |
| 7,401,703 B2 | 7/2008 | McMichael et al. |
| 7,452,346 B2 | 11/2008 | Axelsson |
| 7,452,354 B2 | 11/2008 | Bright et al. |
| 7,497,848 B2 | 3/2009 | Leinsing et al. |
| 7,497,849 B2 | 3/2009 | Fangrow, Jr. |
| 7,530,546 B2 | 5/2009 | Ryan et al. |
| 7,547,302 B2 | 6/2009 | Porto et al. |
| 7,563,243 B2 | 7/2009 | Mendels |
| 7,569,045 B2 | 8/2009 | Deniega et al. |
| 7,578,803 B2 | 8/2009 | Rome et al. |
| 7,584,767 B2 | 9/2009 | Funamura et al. |
| 7,594,910 B2 | 9/2009 | Butts et al. |
| 7,611,503 B2 | 11/2009 | Spohn et al. |
| 7,614,123 B2 | 11/2009 | Schweikert |
| 7,628,779 B2 | 12/2009 | Aneas |
| 7,632,260 B2 | 12/2009 | Antoine |
| 7,637,893 B2 | 12/2009 | Christensen et al. |
| 7,691,090 B2 | 4/2010 | Belley et al. |
| 7,708,027 B2 | 5/2010 | Yokota et al. |
| 7,766,304 B2 | 8/2010 | Phillips |
| 7,892,181 B2 | 2/2011 | Christensen et al. |
| 2002/0002351 A1 | 1/2002 | Cote et al. |
| 2002/0153503 A1 | 10/2002 | Newton et al. |
| 2002/0198458 A1 | 12/2002 | Tripp et al. |
| 2003/0040769 A1 | 2/2003 | Kelley et al. |
| 2003/0165647 A1 | 9/2003 | Kaneko et al. |
| 2003/0173536 A1 | 9/2003 | Christensen et al. |
| 2004/0049157 A1 | 3/2004 | Plishka et al. |
| 2004/0078026 A1 | 4/2004 | Wagner |
| 2004/0082923 A1 | 4/2004 | Field |
| 2004/0116894 A1 | 6/2004 | DeLegge |
| 2004/0209801 A1 | 10/2004 | Brand et al. |
| 2004/0215155 A1 | 10/2004 | Wolfe et al. |
| 2004/0267163 A1 | 12/2004 | Opie et al. |
| 2005/0000975 A1 | 1/2005 | Carco et al. |
| 2005/0025816 A1 | 2/2005 | Tanaka |
| 2005/0090805 A1 | 4/2005 | Shaw et al. |
| 2005/0121638 A1 | 6/2005 | Doyle |
| 2005/0131357 A1 | 6/2005 | Denton et al. |
| 2005/0143691 A1 | 6/2005 | Picha et al. |
| 2005/0203463 A1 | 9/2005 | Lampropoulos |
| 2005/0203597 A1 | 9/2005 | Yamazaki et al. |
| 2005/0209572 A1 | 9/2005 | Rome et al. |
| 2005/0209581 A1 | 9/2005 | Butts et al. |
| 2005/0251102 A1 | 11/2005 | Hegland et al. |
| 2005/0261636 A1 | 11/2005 | Rome et al. |
| 2005/0261664 A1 | 11/2005 | Rome et al. |
| 2005/0267445 A1 | 12/2005 | Mendels |
| 2005/0267487 A1 | 12/2005 | Christensen et al. |
| 2005/0281822 A1 | 12/2005 | Cedarbaum et al. |
| 2006/0009801 A1 | 1/2006 | McGurk et al. |
| 2006/0015086 A1 | 1/2006 | Rasmussen et al. |
| 2006/0025816 A1 | 2/2006 | Shelton |
| 2006/0058702 A1 | 3/2006 | Christensen et al. |
| 2006/0079853 A1 | 4/2006 | Christensen et al. |
| 2006/0092109 A1 | 5/2006 | Hsu et al. |
| 2006/0116721 A1 | 6/2006 | Yun et al. |
| 2006/0118749 A1 | 6/2006 | Ryan et al. |
| 2006/0129109 A1 | 6/2006 | Shaw et al. |
| 2006/0200089 A1 | 9/2006 | Lopez et al. |
| 2006/0211998 A1 | 9/2006 | Fangrow |
| 2006/0211999 A1 | 9/2006 | Fangrow |
| 2006/0212000 A1 | 9/2006 | Fangrow |
| 2006/0212001 A1 | 9/2006 | Fangrow |
| 2006/0212002 A1 | 9/2006 | Fangrow |
| 2006/0212003 A1 | 9/2006 | Fangrow |
| 2006/0264842 A1 | 11/2006 | Fangrow |
| 2007/0038143 A1 | 2/2007 | Christensen et al. |
| 2007/0073270 A1 | 3/2007 | Christensen et al. |
| 2007/0083157 A1 | 4/2007 | Belley et al. |
| 2007/0083162 A1 | 4/2007 | O'Reagan et al. |
| 2007/0100295 A1 | 5/2007 | Belley et al. |
| 2007/0100322 A1 | 5/2007 | Venugopalan et al. |
| 2007/0235674 A1 | 10/2007 | Vangsness et al. |
| 2007/0235675 A1 | 10/2007 | Kimball et al. |
| 2007/0235676 A1 | 10/2007 | Vangsness et al. |
| 2007/0255167 A1 | 11/2007 | Christensen et al. |
| 2007/0255229 A1 | 11/2007 | Kane et al. |
| 2007/0260195 A1 | 11/2007 | Bartholomew et al. |
| 2008/0091174 A1 | 4/2008 | Alam et al. |
| 2008/0097407 A1 | 4/2008 | Plishka |
| 2008/0103408 A1 | 5/2008 | Denton et al. |
| 2008/0114316 A1 | 5/2008 | Christensen et al. |
| 2008/0177175 A1 | 7/2008 | Mottola et al. |
| 2008/0277610 A1 | 11/2008 | Bahner et al. |
| 2009/0043270 A1 | 2/2009 | Noyce et al. |
| 2009/0219353 A1 | 9/2009 | Price et al. |
| 2009/0261130 A1 | 10/2009 | Pittl et al. |
| 2009/0314973 A1 | 12/2009 | Christensen et al. |
| 2010/0030163 A1 | 2/2010 | Carrez et al. |
| 2010/0044609 A1 | 2/2010 | Matsubara |
| 2011/0083665 A1 | 4/2011 | Denton et al. |

FOREIGN PATENT DOCUMENTS

| | | |
|---|---|---|
| DE | 9105229 U1 | 6/1991 |
| DE | 4311715 A1 | 10/1994 |
| EP | 0270205 A2 | 6/1988 |
| EP | 0829248 A2 | 3/1998 |
| EP | 1547537 A1 | 6/2005 |
| EP | 1740253 A1 | 1/2007 |
| EP | 1782850 A1 | 5/2007 |
| FR | 2551978 A2 | 3/1985 |
| GB | 2394761 A | 5/2004 |
| JP | 2002-049660 A | 2/1990 |
| JP | 2005-115556 A | 5/1993 |
| JP | H6-504468 T | 5/1994 |
| JP | H6-66642 | 9/1994 |
| JP | 2000-517216 T | 12/2000 |
| JP | 2002-177379 A | 6/2002 |
| WO | 9911192 A1 | 3/1999 |
| WO | 0204065 A2 | 1/2002 |
| WO | 03001993 A2 | 1/2003 |
| WO | 03018105 A1 | 3/2003 |
| WO | 2005007213 A2 | 1/2005 |
| WO | 2005044716 A2 | 5/2005 |

| | | | |
|---|---|---|---|
| WO | 2005052366 A2 | 6/2005 |
| WO | 2005099805 A1 | 10/2005 |
| WO | 2005107843 A1 | 11/2005 |
| WO | 2006004943 A2 | 1/2006 |
| WO | 2006055288 A2 | 5/2006 |
| WO | 2006060248 A2 | 6/2006 |
| WO | 2006066023 A2 | 6/2006 |
| WO | 2007038643 A1 | 4/2007 |
| WO | 2007116386 A1 | 10/2007 |
| WO | 2008115439 A1 | 9/2008 |
| WO | 2008142580 A2 | 11/2008 |
| WO | 2009081180 A1 | 7/2009 |
| WO | 2009118521 A1 | 10/2009 |
| WO | 2010028044 A1 | 3/2010 |
| WO | 2010091356 A1 | 8/2010 |

OTHER PUBLICATIONS

"Pleurodesis," ASAP, vol. 118, No. 3, p. 577, Sep. 1, 2000.
AstraTech Healthcare, "Premium Wound Drainage Products," http://surgery.astratech.com/Main.aspx? Item=155788&navt=5&navl=82118&nava=81296, copyright 2010, printed Oct. 28, 2010.
Bard Access Systems, Inc., "Poly Per-Q-Cath PICC Catheter with Safety Excallibur Introducer," Instructions for Use, May 2003.
Bard, "Groshong NXT PICC Instructions for Use," Product Brochure, Nov. 2003.
Bellamy, R.F., "The Causes of Death in Conventional Land Warfare: Implications for Combat Casualty Care Research." Mil. Med., vol. 149, pp. 55-62, 1984.
Bilski, T.R., et al., "Battlefield Casualties Treated at Camp Rhino, Afghanistan: Lessons Learned", J. Trauma, vol. 54, No. 5, pp. 814-822, May 2003.
Campisi, P., et al., "Outpatient Treatment of Spontaneous Pneumothorax in a Community Hospital Using a Heimlich Flutter Valve: A Case Series." The Journal of Emergency Medicine, vol. 15, No. 1, pp. 115-119, 1997.
Denver Biomedical, "Pleurx Drainage Kit Catalog No. 50-7500," Instructions for Use.
EP 04811627.1 Supplementary European Search Rerpot dated Oct. 22, 2010.
Groves Jr., "Operations in Urban Enviornments", Military Review, vol. 78, No. 4, Jul./Aug. 1998.
Heimlich, H.J., "Valve Drainage of the Pleural Cavity." Diseases of the Chest, vol. 53, No. 3, pp. 282-287, 1968.
Hewitt at al. "A Management Strategy for Malignancy-Induced Pleural Effusion: Long-term Thoracostomy Drainage." ONF, vol. 14, No. 5, 1987, pp. 17-22.
ICU-USA, "Wound Drainage," www.icu-usa.com/tour/procedures/drains.htm, copyright 1999-2004, printed Oct. 28, 2010.
ISO 10079-2 Medical Suction Equipment—Part 2: Manually Powered Suction Equipment, International Standard Organization 1999 (E).
Jaskille, et al., "A Portable Handpump is Effective in the Evacuation of Hemothorax in a Swine Model of Penetrating Chest Injury." The Journal of Trauma Injury, Infection, and Critical Care, Nov. 2003, pp. 864-868.
JP 06-541538 filed Nov. 22, 2004 Summarized Translation of Notice of Rejection (Office Action) dated Mar. 2, 2010.
JP 06-541538 filed Nov. 22, 2004 Summarized Translation of Notice of Rejection (Office Action) dated Jun. 23, 2009.
JP 06-541538 filed Nov. 22, 2004 Summarized Translation of Notice of Rejection (Office Action) dated Oct. 1, 2010.
Light, R.W. et al., "A Single Intrapleural Injection of Transforming Growth Factor-Beta(2) Produces an Excellent Pleurodesis in Rabbits." Am. J. Respir. Crit. Care Med., vol. 162, No. 1, pp. 98-104, 2000.
Light, R.W. et al., "Talc Slurry is an Effective Pleural Sclerosant in Rabbits." Chest, vol. 106, No. 6, pp. 1702-1706, 1995.
Lodi, R., et al., "A New Portable Chest Drainage Device." Ann. Thorac. Surg., vol. 69, pp. 998-1000, 2000.
Mabry, R.L., et al., "United States Army Rangers in Somalia: An Analysis of Combat Casualties on an Urban Battlefield", J. Trauma. vol. 49, No. 3, pp. 515-529, Sep. 2000.
MEDCOMP ASH II Split Cathä "Features and Benefits" product brochure.
Medcompare, "Drains with Reservoirs," General Surgery Product Matrix, Medompare.com/matrix/1885/Drains-with-Reservoirs.html, copyright 2003-2010, printed Oct. 28, 2010.
Milton, Jr., T.R., "Urban Operations: Future War", Military Review, vol. 74, Issue 2, Feb. 1994.
Montes, J.F. et al., "Influence of Talc Dos on Extrapleural Talc Dissemination after Talc Pleurodesis." Am. J. Respir. Crit. Care Med., vol. 168, No. 3, pp. 348-355, 2003.
Ohm, et al. "Use of Indwelling Pleural Catheter Comparaed with Thorascopic Talc Pleurodesis in the Management of Malignant Pleural Effusions." Division of Thoracic Surgery and Department of Surgery, William Beaumont Hospital, The American Surgeon Mar. 2003, vol. 69, pp. 198-202.
PCT/US04/38937 filed Nov. 22, 2004 Preliminary Report on Patentability dated Jul. 5, 2005.
PCT/US04/38937 filed Nov. 22, 2004 Search Report dated Jul. 5, 2005.
PCT/US2006/037766 filed Sep. 26, 2006 Preliminary Report on Patentability dated Mar. 26, 2008.
PCT/US2006/037766 filed Sep. 26, 2006 Search Report dated Jan. 25, 2007.
PCT/US2006/037766 filed Sep. 26, 2006 Written Opinion dated Mar. 26, 2008.
Pope, A., et al., "Fluid Resuscitation: State of the Science for Treating Combat Casualties and Civilian Injuries." National Academy Press, 1999.
Schweitzer, E.F. et al., "Use of Heimlich Valve in Compact Autotransfusion Device." The Journal of Trauma, vol. 27, No. 5, pp. 537-542, 1987.
Tremblay, A. et al., "Single-Center Experience with 250 Tunnelled Pleural Catheter Insertions for Malignant Pleural Effusion." Chest, vol. 129, No. 2, pp. 362-368, 2006.
U.S. Appl. No. 10/595,450, filed Jun. 21, 2007, titled Portable Hand Pump for Evacuation of Fluids, listing Hasan B. Alam, Peter Rhee and Emily Rhee as inventors.
U.S. Appl. No. 10/595,450, filed Jun. 21, 2007 Office Action dated Apr. 9, 2010.
U.S. Appl. No. 10/595,450, filed Jun. 21, 2007 Office Action dated Jul. 7, 2009.
U.S. Appl. No. 10/595,450, filed Jun. 21, 2007 Office Action dated Oct. 1, 2010.
U.S. Appl. No. 10/595,450, filed Jun. 21, 2007 Office Action dated Oct. 30, 2008.
U.S. Appl. No. 11/248,082, filed Oct. 12, 2005 Restriction Requirement dated Jan. 20, 2008.
U.S. Appl. No. 11/248,082, filed Oct. 12, 2005, Notice of Allowance dated Jan. 12, 2010.
U.S. Appl. No. 11/248,082, filed Oct. 12, 2005, Notice of Allowance dated Oct. 15, 2010.
U.S. Appl. No. 11/248,082, filed Oct. 12, 2005, Office Action dated Mar. 30, 2010.
U.S. Appl. No. 11/248,082, filed Oct. 12, 2005, Office Action dated Jun. 29, 2009.
U.S. Appl. No. 11/248,082, filed Oct. 12, 2005, Office Action dated Oct. 30, 2008.
U.S. Appl. No. 11/535,245, filed Sep. 26, 2006 Non-Final Office Action dated Oct. 12, 2010.
Vargas, F.S. et al., "Comparison of Silver Nitrate and Tetracycline as Pleural Sclerosing Agents in Rabbits." Chest, vol. 108, No. 4, pp. 1080-1083, 1995.
CA 2546434 filed Nov. 22, 2004 Office Action dated Dec. 15, 2010.
EP 04811627.1 filed Nov. 22, 2004 Office Action dated Feb. 23, 2011.
U.S. Appl. No. 11/248,082, filed Oct. 12, 2005 Non-Final Office Action dated Dec. 21, 2010.
U.S. Appl. No. 11/535,245, filed Sep. 26, 2006 Final Office Action dated Mar. 17, 2011.
U.S. Appl. No. 11/248,082, filed Oct. 12, 2005 Non-Final Office Action dated Jul. 6, 2011.
U.S. Appl. No. 11/535,245, filed Sep. 26, 2006 Non-Final Office Action dated Jul. 7, 2011.
U.S. Appl. No. 12/188,955, filed Aug. 8, 2008 Non-Final Office Action dated Aug. 26, 2011.

\* cited by examiner

CATHETER CONNECTION SYSTEMS

PRIORITY

This application is a continuation of U.S. patent application Ser. No. 11/535,245, filed Sep. 26, 2006, which claims priority to U.S. Provisional Patent Application No. 60/720,443, filed Sep. 26, 2005, each of which is incorporated by reference into this application as if fully set forth herein.

BACKGROUND OF THE INVENTION

Catheters may be employed for draining fluids from various organs or other locations within a patient. For example, catheters may be used for draining urine, a surgical wound, or any other body location that may be beneficial. Further, it may be desirable to selectively couple and decouple such a catheter to and from a drainage system or other system (e.g., aspiration system, cleansing system, etc.), respectively, for cleaning or for any other suitable reason. Such a connection system can enable an increase in ambulation for the patient and thereby increase quality of life.

BRIEF SUMMARY

One aspect of the instant disclosure relates to a catheter connection system comprising at least two components and a deformable sealing element positioned between the at least two components configured to allow, upon deformation, fluid flow through the at least two components. Another aspect of the instant disclosure relates to a catheter connection system comprising a sealing element positioned between at least two components, wherein the components are coupled to one another by a locking member.

Features from any of the above-mentioned embodiments may be used in combination with one another in accordance with the instant disclosure. In addition, other features and advantages of the instant disclosure will become apparent to those of ordinary skill in the art through consideration of the ensuing description, the accompanying drawings, and the appended claims.

BRIEF DESCRIPTION OF THE DRAWINGS

Advantages of the present invention will become apparent upon review of the following detailed description and drawings, which illustrate representations (not necessarily drawn to scale) of various embodiments of the invention, wherein.

DETAILED DESCRIPTION

One aspect of the instant disclosure relates to apparatuses and systems for selective coupling of a tubular member to another tubular element. Specifically, the instant disclosure contemplates that a catheter may include a connection structure for selectively coupling the catheter to another tubular element by way of a sealing element that forms a seal between the catheter and tubular element.

Figure 1:
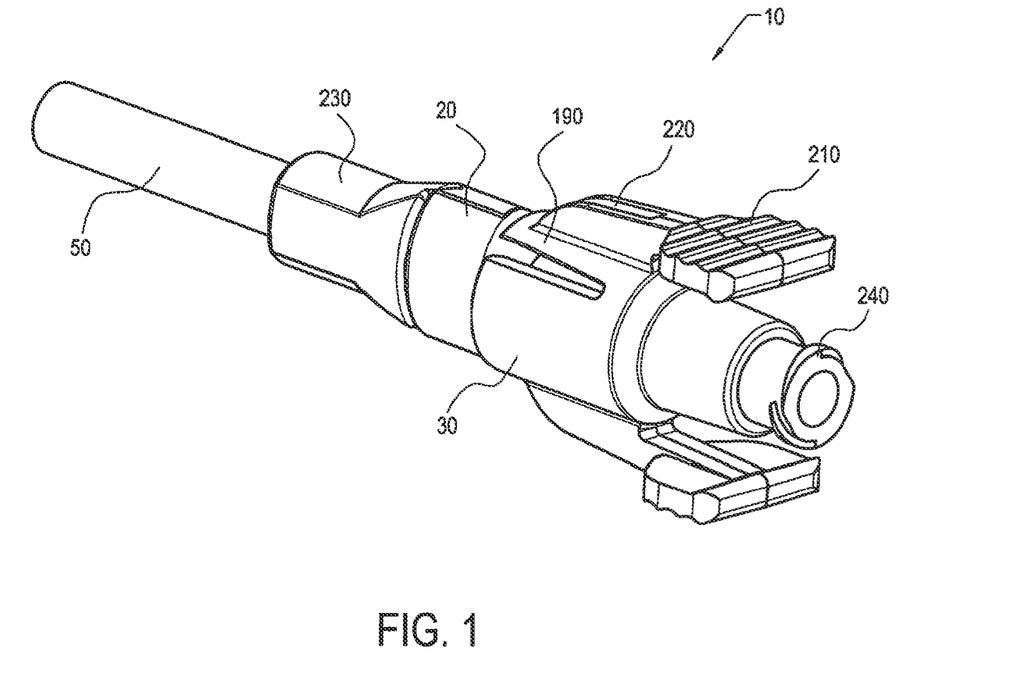
FIG. 1 is a perspective view of one embodiment of a catheter coupling system.
Figure 2:
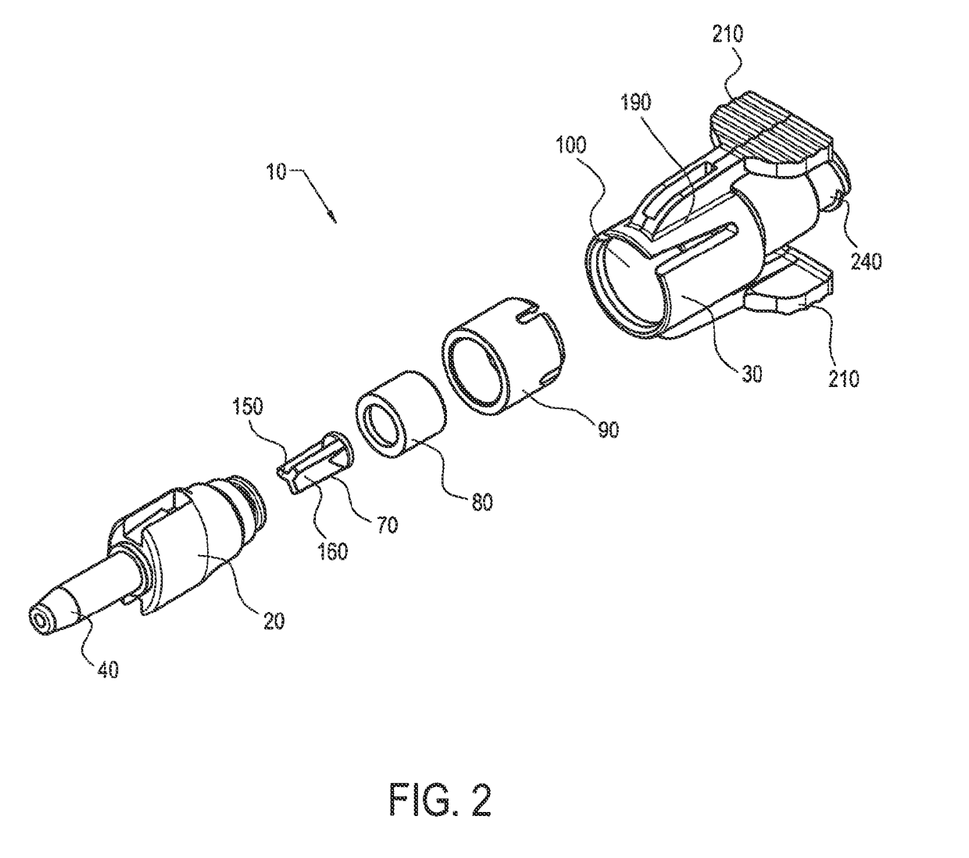
FIG. 2 is an exploded view of the catheter coupling system of FIG. 1.

One aspect of the present invention, as shown in FIG. 1, includes a catheter connection system 10 comprising a catheter hub 20, a coupling member 30, and at least one deformable sealing element positioned within the catheter hub. The deformable sealing element is configured to allow fluid flow through catheter hub 20 upon deformation. As illustrated in FIGS. 1 through 3b, the catheter connector system 10 comprises catheter hub 20 having a cannula 40 on a proximal end thereof sized for insertion into a lumen of a catheter 50, and a housing 45 on a distal end thereof. Further, catheter hub 20 has a distal interface 60 having a seal post 70 positioned within a deformable sealing element 80 positioned further within a retention collar 90. As illustrated in FIG. 2, the coupling member 30 includes a cavity 100 for receiving at least a portion of the distal interface 60 of catheter hub 20 and an actuating member 110 for engaging at least a portion of deformable sealing element 80.

Figure 3A:
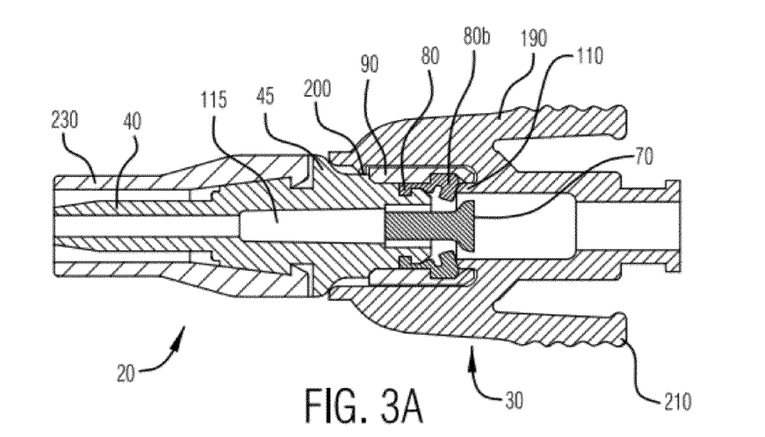
FIG. 3a is a side, cross-sectional view of the catheter coupling system shown in FIG. 1.
Figure 3B:
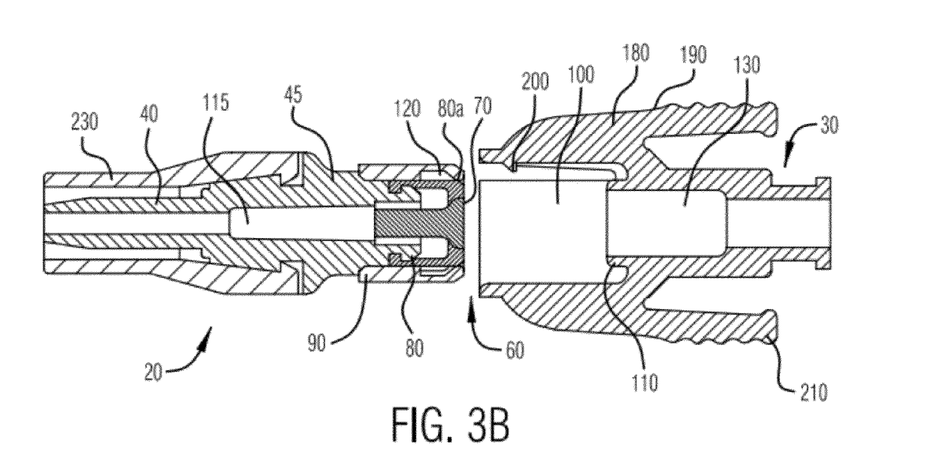
FIG. 3b is a side, cross-sectional view of the catheter coupling system shown in FIG. 1 but with the catheter hub disconnected from the coupling member.

Referring now to FIGS. 3a and 3b, deformable sealing element 80 may abut seal post 70 to effectively seal a bore 115 of catheter hub 20 at one end. In an unbiased position 80a, deformable sealing element 80 creates a seal wherein any fluids attempting to pass through catheter hub 20 are precluded from movement past the seal. When engaged by coupling member 30, deformable sealing element 80 deforms to a biased position 80b thereby allowing fluid to flow through or by deformable sealing element 80 and into coupling member 30. When coupling member 30 is removed from catheter hub 20, deformable sealing element 80 reversibly returns to its unbiased position 80a. The ability of deformable sealing element 80 to reversibly return to its unbiased position 80a permits reuse of catheter hub 20. Furthermore, it advantageously creates a flush surface which facilitates cleaning of distal interface 60 of catheter hub 20. Referring now to FIGS. 3a and 3b, catheter hub 20 can further comprise an open space 120 between retention collar 90 and deformable sealing element 80. Open space 120 provides an area for deformable sealing element 80 to deform when it is engaged by coupling member 30. In one aspect of the invention, retention collar 90 may extend beyond deformable sealing element 80 and seal post 70. Such a configuration may minimize inadvertent deformation of deformable sealing element 80 by a user.

In one embodiment, actuating member 110 can be disposed concentrically within cavity 100. Further, coupling member 30 can be configured with a through-center bore 130 for communicating a fluid from catheter hub 20 through coupling member 30. In an additional embodiment, actuating member 110 comprises a raised surface located within cavity 100 of coupling member 30. The raised surface of actuating member 110 can be shaped to approximate the shape of deformable sealing element 80 such that when coupling member 30 and catheter hub 20 are secured together, as shown in FIG. 3a, actuating member 110 deforms deformable sealing element 80 thereby allowing fluid to pass through catheter hub 20 and into coupling member 30. In another embodiment, actuating member 110 may be configured to deform only a portion of deformable sealing element 80.

Figure 4:
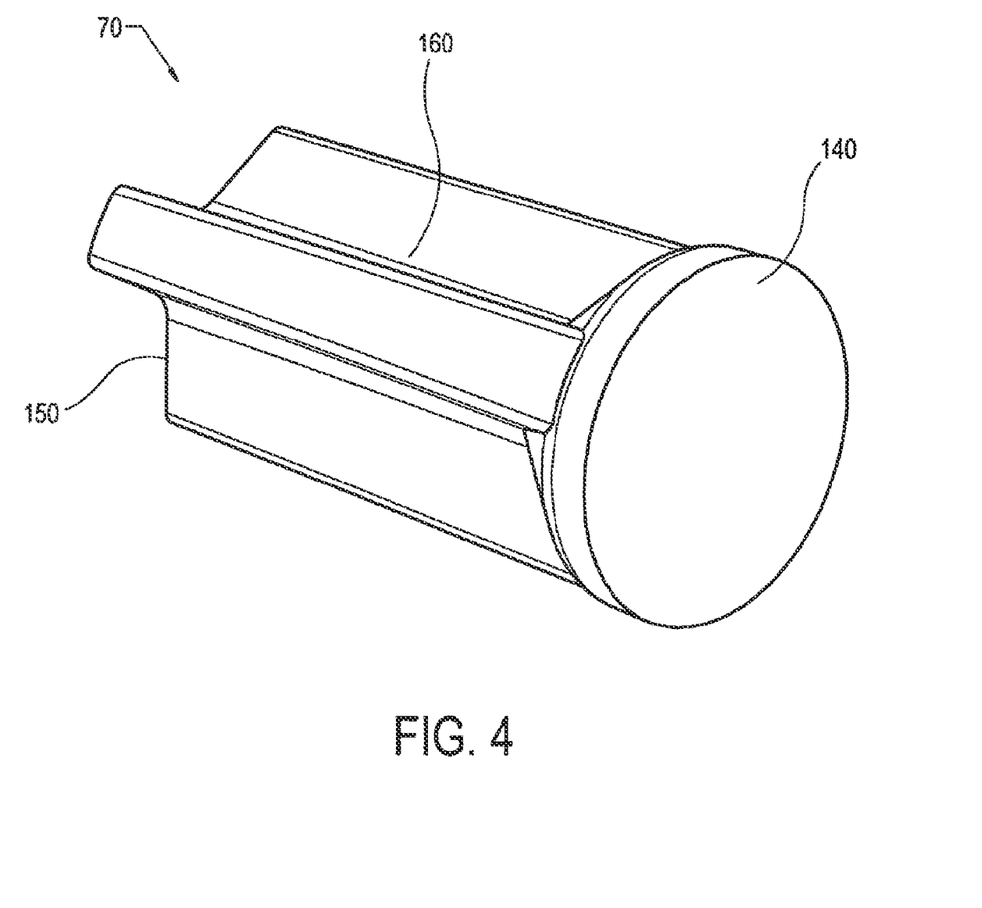
FIG. 4 is a perspective view of one embodiment of a seal post.

In an additional embodiment, seal post 70 may be positioned near deformable selling sealing element 80 to facilitate deformation of deformable sealing element 80 and passage of fluids through catheter hub 20 to coupling member 30. In one embodiment, as shown in FIG. 4, seal post 70 comprises a top planar surface 140 that, when seated in the body of catheter hub 20 and within the center of deformable sealing element 80, creates a flush surface. The body of seal post 70 can be tapered such that the diameter of a distal top planar surface 140 is larger than the diameter of the proximal end 150 of seal post 70. The body of seal post 70 can also comprise at least one channel 160, wherein, when deformable sealing element 80 is deformed, fluid passes through channel 160 of seal post 70 and into coupling member 30. In such a configuration, seal post 70 can be affixed (e.g., adhesively bonded, ultrasonically welded, solvent welded, or otherwise affixed) to the body of catheter hub 20. In another embodiment, seal post 70 may be formed integrally or monolithically with the body of catheter hub 20.

In another embodiment of the present invention, coupling member 30 and catheter hub 20 may be secured together with a locking member 180. The locking member 180 may be any device for securing catheter hub 20 and the coupling member 30 together, for example, a so-called "living hinge clip" or any cantilevered pivoting element. FIGS. 1-3b illustrate a coupling member 30 comprising a biased hinge member 190 integrally formed with the wall of coupling member 30. The hinge member 190 includes an engagement feature 200 configured to engage at least a portion of retention collar 90 of the body of catheter hub 20. Additionally, handles 210 may be formed with hinge member 190 to facilitate removal and attachment of coupling member 30. In one aspect of the invention, as shown in FIGS. 1 and 2, the catheter connection system 10 may comprise an aperture 220 positioned on an outer portion of coupling member 30. Advantageously, aperture 220 allows the user to verify engagement of deformable sealing element 80 by actuating member 110. In another embodiment, the catheter hub 20 also comprises a cover member 230 configured to reduce the likelihood of accidental removal of catheter 50 from cannula 40 of catheter hub 20. A proximal end of coupling member 30 may further comprise a luer fitting 240 configured to receive a device, for example, for vacuum assisted removal of fluids from the patient. In another embodiment, the proximal end of coupling member 30 may be configured for gravity evacuation of fluids from the patient.

The catheter hub 20 and coupling member 30 described above can be formed from any material suitable for connection to any elongated tubular member placed within the corpus of a patient. By way of example, the connector system 10 may be prepared from of any suitable thermo-plastically formed material. The deformable sealing element 80 can be formed from a resilient material that is flexible, inert, and impermeable to fluid, such as silicone or polyurethane.

The above embodiments may be used, for example, in connection with a pleural drainage system. One example of components of a pleural drainage system are disclosed in U.S. patent application Ser. No. 10/595,450 entitled "Portable Hand Pump for Evacuation of Fluids" which is incorporated herein in its entirety. More specifically, the present invention may be used to connect a catheter placed within the corpus of a patient for the purposes of evacuating fluid from the corpus of the patient to a manually-operated pump and a device for storage of the evacuated fluid. The pump may be adapted to connect to an inflow conduit and an outflow conduit. For purposes of clarity, the pump, outflow conduit, and inflow conduit are all downstream from the connection system of the present invention. Near the connection of the inflow conduit, the pump can be provided with a one-way inflow valve that acts to permit flow of fluids from the inflow conduit into the interior of the pump but limits or restricts any back flow of the same into the inflow conduit. Similarly, near the connection of the outflow conduit, a one-way outflow valve permits flow of fluids out of the pump interior and into and through a lumen of the outflow conduit. This outflow one-way valve also serves to limit or restrict the back flow of fluids from the outflow conduit into the pump interior.

While certain embodiments and details have been included herein for purposes of illustrating aspects of the instant disclosure, it will be apparent to those skilled in the art that various changes in the systems, apparatuses, and methods disclosed herein may be made without departing from the scope of the instant disclosure, which is defined, in part, in the appended claims. The words "including" and "having," as used herein including the claims, shall have the same meaning as the word "comprising."

What is claimed is:

1. A catheter connector system, comprising:
 a catheter hub, comprising:
  a cannula on a proximal end of the catheter hub sized for insertion into a lumen of a first tubular element,
  a bore to communicate a fluid from the cannula through the first tubular element,
  a housing on a distal end of the catheter hub, and
  a distal interface having:
   a retention collar,
   a deformable sealing element positioned within the retention collar, and
   a tapered seal post longitudinally fixed relative to the catheter hub and positioned within the deformable sealing element,
   each of the retention collar, deformable sealing element, and tapered seal post extending past a distal end of the housing; and
 a coupling member, comprising:
  a cavity receiving at least a portion of the distal interface of the catheter hub,
  at least one locking member formed on an outer surface of the cavity, the locking member having a ledge formed on an inner surface of the cavity to engage at least a portion of the retention collar,
  an actuating member disposed within the cavity to engage at least a portion of the deformable sealing element, and
  a bore to communicate a fluid from the catheter hub through the coupling member into a second tubular element.

2. The catheter connector system of claim 1, wherein the cavity, the deformable sealing element, the distal interface of the catheter hub, the retention collar, and the actuating member are substantially annular.

3. The catheter connector system of claim 1, wherein the locking member and the ledge are integrally formed on the surface of the cavity.

4. The connector system of claim 1, wherein the deformable sealing element surrounds and abuts the seal post to seal a bore of the connector hub.

5. The connector system of claim 4, the connector system comprising a sealed configuration where a sealing surface of the deformable sealing element is in contact with the seal post to prevent fluid flow through the connector hub, and an open configuration where the deformable sealing element is deformed such that the sealing surface is longitudinally displaced with respect to the connector hub and the seal post to open a fluid flow path through the connector hub.

6. The catheter connector system of claim 1, wherein a distal end of the tapered seal post, deformable sealing element, and retention collar are longitudinally co-extensive in a sealed position.

7. The catheter connector system of claim 6, wherein the deformable sealing element is retained between the retention collar and the housing of the catheter hub to longitudinally fix a proximal end of the deformable sealing element with respect to the catheter hub.

8. The catheter connector system of claim 7, wherein the retention collar comprises an internal indention creating an open space between the deformable sealing element and the retention collar to provide a volume for the deformable sealing element to deform when engaged by coupling member.

* * * * *